United States Patent [19]

Mandai et al.

[11] Patent Number: 6,075,132
[45] Date of Patent: Jun. 13, 2000

[54] URSODEOXYCHOLIC ACID DERIVATIVES AND METHODS FOR PRODUCING THEM

[75] Inventors: Tadakatsu Mandai, Okayama; Hiroshi Okumoto, Okayama-ken; Katsuyoshi Nakanishi, Yokohama; Koji Hara, Yokohama; Katsuhiko Mikuni, Yokoyama; Kozo Hara, Yokohama; Teruhiko Umetsu, Tokyo, all of Japan

[73] Assignees: Bio Research Corporation of Yokohama; Ensuiko Sugar Refining Co., Ltd., both of Yokohama; Kaken Pharmaceutical Co., Ltd., Tokyo, all of Japan

[21] Appl. No.: 09/069,990

[22] Filed: Apr. 30, 1998

[30] Foreign Application Priority Data

Jan. 8, 1998 [JP] Japan .................................. 10-013172

[51] Int. Cl.⁷ ...................................................... C07J 17/00
[52] U.S. Cl. ................................................. 536/5; 514/26
[58] Field of Search .................................. 514/26; 536/5

[56] References Cited

U.S. PATENT DOCUMENTS

| 4,157,894 | 6/1979 | Bombardelli | 23/230 R |
| 4,229,441 | 10/1980 | Bugianesi et al. | 514/26 |
| 4,548,922 | 10/1985 | Carey et al. | 514/4 |
| 4,652,553 | 3/1987 | Hagmann et al. | 514/26 |
| 4,942,154 | 7/1990 | Durette et al. | 514/26 |
| 4,970,199 | 11/1990 | Durette et al. | 514/26 |
| 5,338,837 | 8/1994 | Kahne | 536/5 |
| 5,455,335 | 10/1995 | Kahne et al. | 536/5 |
| 5,502,038 | 3/1996 | Malinow | 514/26 |
| 5,571,795 | 11/1996 | Kahne et al. | 514/26 |
| 5,627,270 | 5/1997 | Kahne et al. | 536/5 |
| 5,693,769 | 12/1997 | Kahne et al. | 536/5 |
| 5,747,445 | 5/1998 | Bäckström et al. | 514/4 |
| 5,763,582 | 6/1998 | Rao et al. | 536/5 |
| 5,770,578 | 6/1998 | Binder et al. | 514/26 |

FOREIGN PATENT DOCUMENTS

| 9311772 | 6/1993 | WIPO . |
| 9529186 | 11/1995 | WIPO . |
| 9600230 | 1/1996 | WIPO . |

OTHER PUBLICATIONS

Cheng et al., "Facial Ampliphiles," *J. Amer. Chem. Soc.,* 114(18), 7319–7320 (Aug. 26, 1992).

Venkatesan et al., "Hydrogen Bonding in Micelle Formation," *J. Amer. Chem. Soc.,* 116(15), 6955–6956 (Jul. 27, 1994).

Walker et al., "Cationic Facial Amphiphiles: A Promising Class of Transfection Agents," *Proc. Natl. Acad. Sci. USA,* 93, 1585–1590 (Feb. 20, 1996).

Bowe et al., "Design of Compounds That Increase the Adsorption of Polar Molecules," *Proc. Natl. Acad. Sci. USA,* 94, 12218–12223 (Oct. 28, 1997).

*Primary Examiner*—Cecilia Tsang
*Assistant Examiner*—L. Eric Crane
*Attorney, Agent, or Firm*—Oblon, Spivak, McClelland, Maier & Neustadt, P.C.

[57] ABSTRACT

Disclosed are ursodeoxycholic acid derivatives having an increased solubility in water, and methods for producing the derivatives. To produce the derivatives, ursodeoxycholic acid is protected at its carboxyl group with a benzyl group, then reacted with tetrabenzyl-acetic acid-oxyglucoside of the following formula (1), and de-benzylated; or ursodeoxycholic acid is protected at its hydroxyl group with a t-butyldimethylsilyl group, then reacted with tetrabenzyl-2-hydroxyethyloxyglucoside of the following formula (2), and de-t-butyldimethylsilylated and de-benzylated.

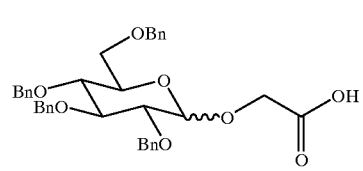

(1)

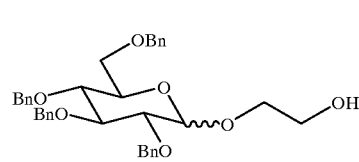

(2)

9 Claims, No Drawings

US 6,075,132

URSODEOXYCHOLIC ACID DERIVATIVES AND METHODS FOR PRODUCING THEM

FIELD OF THE INVENTION

The present invention relates to ursodeoxycholic acid derivatives and methods for producing them. Precisely, it relates to ursodeoxycholic acid derivatives having a saccharide moiety as bonded to ursodeoxycholic acid via a spacer therebetween and having improved solubility in water, and to methods for producing them.

BACKGROUND OF THE INVENTION

Ursodeoxycholic acid is one type of bile acids found in bear bile, and has been known to have a cholagogic effect as its pharmaceutical activity. Tablets containing the compound are commercially available. However, as the compound is hardly soluble in water (38 $\mu$g/ml), its use is limited. Improving its solubility in water will make the compound usable in injections, which may be applied even to postoperated-patients and to patients to whom drugs cannot be orally administered.

Accordingly, it is desired to develop a method for improving the solubility of ursodeoxycholic acid in water.

Known is glycosyiation as one means for improving the solubility of hardly-soluble substances.

For chemical glycosylation, various methods are known such as those described in Experimental Chemical Lectures 26, 4th Edition, "Organic synthesis VIII, Chapter 3", edited by the Chemical Society of Japan. However, all the known methods are disadvantageous for industrialization, as using strong Lewis acids. On the other hand, glycosylation with enzyme, if applied to ursodeoxycholic acid, is problematic in that only small amounts of products could be obtained as the solubility of the substrate, ursodeoxycholic acid in water is very low.

SUMMARY OF THE INVENTION

Given the situation noted above, we, the present inventors have assiduously studied, and have found a method of binding a saccharide molecule to the hydroxyl or carboxyl group of ursodeoxycholic acid via a spacer therebetween, and have further found that the method is effective in improving the intended physical property of the compound. On the basis of these findings, we have completed the present invention.

Specifically, the invention provides ursodeoxycholic acid derivatives having a saccharide moiety as bonded to ursodeoxycholic acid via a spacer therebetween.

Preferably, the spacer in the ursodeoxycholic acid derivatives is a glycolate or glycol.

Preferred embodiments of the ursodeoxycholic acid derivatives include diglycosyloxyacetyl-3,7-ursodeoxycholic acid (hereinafter referred to as 3,7-GLG-ursodeoxycholic acid), of a formula:

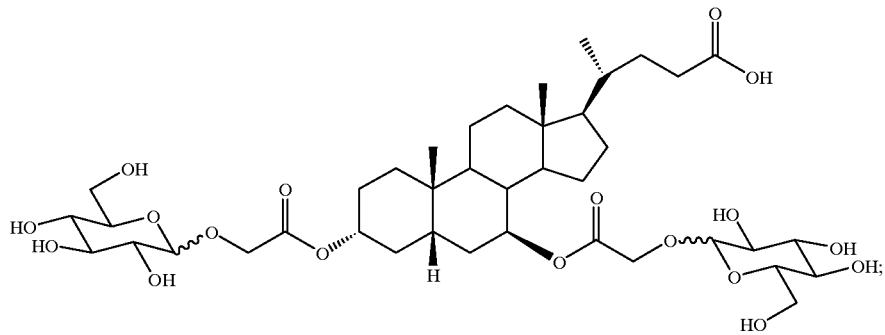

glycosyloxyacetyl-3-ursodeoxycholic acid (hereinafter referred to as 3-GLG-ursodeoxycholic acid) of a formula:

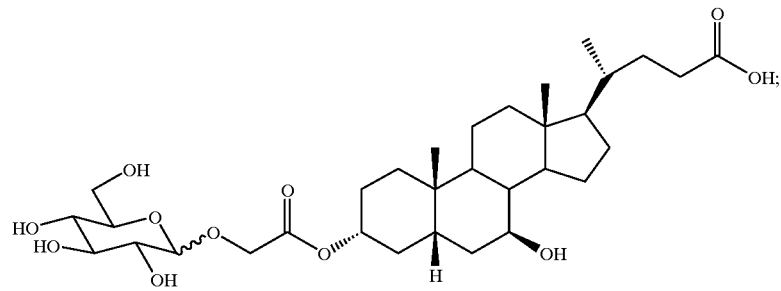

glycosyloxyacetyl-7-ursodeoxycholic acid (hereinafter referred to as 7-GLG-ursodeoxycholic acid) of a formula:

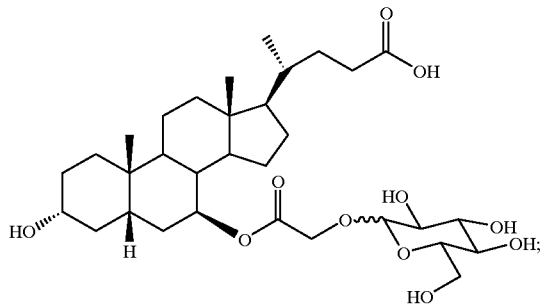

and glycosyloxyethyl-24-ursodeoxycholic acid (hereinafter referred to as 24-GLG-ursodeoxycholic acid) of a formula:

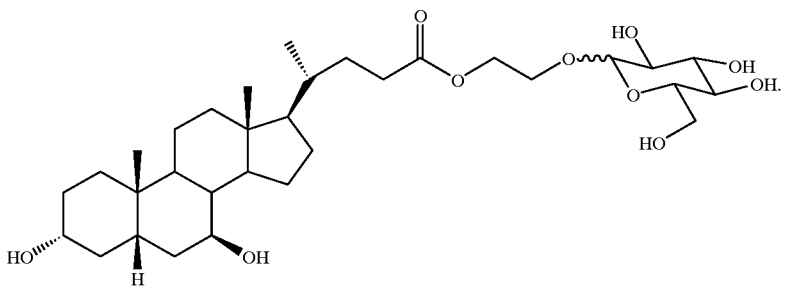

The invention also provides a method for producing the ursodeoxycholic acid derivatives described above, comprising protecting the carboxyl group of ursodeoxycholic acid with a benzyl group, then reacting the acid with tetrabenzyl-acetic acid-oxyglucoside of the following formula, and de-benzylating it.

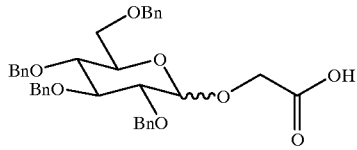

The invention further provides a method for producing the ursodeoxycholic acid derivatives described above, comprising protecting the hydroxyl group of ursodeoxycholic acid with a t-butyldimethylsilyl group, then reacting the acid with tetrabenzyl-2-hydroxyethyloxyglucoside of the following formula, and de-t-butyldimethylsilylating and de-benzylating it.

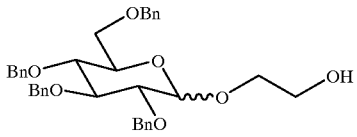

DETAILED DESCRIPTION OF THE INVENTION

Now, the invention is described in detail hereinunder.

As mentioned above, the ursodeoxycholic acid derivatives of the present invention have a saccharide moiety as bonded to one or two hydroxyl groups or to a carboxyl group via a spacer therebetween.

For the reaction to bind a saccharide moiety to ursodeoxycholic acid via a spacer therebetween, used is tetrabenzyl-acetic acid-oxyglucoside or tetrabenzyl-2-hydroxyethyloxyglucoside. The compound, tetrabenzyl-acetic acid-oxyglucoside is prepared by binding a spacer, glycolate such as ethyl glycolate to tetrabenzylglucose, which is obtained from a starting compound of glucose in an ordinary manner, to give an ester, followed by de-ethylating it into the carboxylic acid compound, and is represented by the following formula:

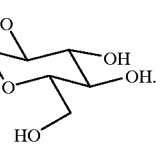

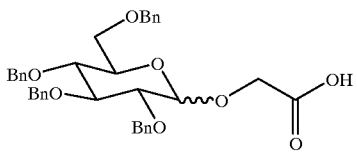

One example of the method for producing tetrabenzyl-acetic acid-oxyglucoside is mentioned below.

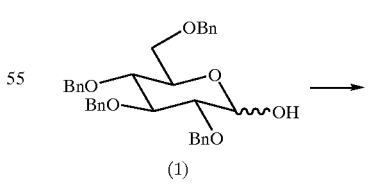

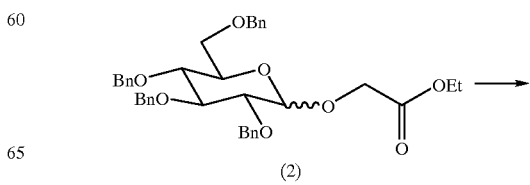

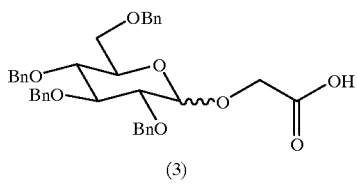

(3)

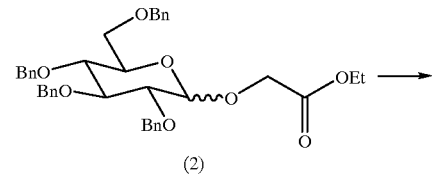

(2)

Precisely, tetrabenzylglucose (1) is reacted with ethyl glycolate along with P-toluenesulfonic acid in benzene at 0 to 150° C., preferably at 110° C., for 0.5 to 50 hours, preferably 8 hours thereby binding ethyl glycolate to the tetrabenzylglucose (1) at its 1-position to obtain aniethyl ester (compound (2) having a molecular weight of 626.76). Next, the compound (2) is processed with a solution of an alkali (e.g., 6N NaOH) in methanol-dioxane at room temperature to 100° C. for 0.5 to 50 hours, preferably 3 hours, and then acidified with hydrochloric acid (e.g., 1N HCl) to de-ethylate it into the corresponding carboxylic acid compound (3). This compound (3) is the intended tetrabenzyl-acetic acid-oxyglucoside.

Using any other saccharides in place of glucose in this reaction gives corresponding saccharide-modified products having different saccharides. Usable saccharides include, for example, mannose and galactose. Intended glycosides are obtainable irrespective of the types of saccharides used, as well known to those skilled in the art, for example, as disclosed by G. N. Bollenback in Methods Carbohydr. Chem., 2, 326 (1963) and by Dwight F. Mowery, Jr. in Methods Carbohydr. Chem., 2, 328 (1963).

In the present invention, used is a glycolate such as ethyl glycolate as the spacer for the saccharide donor. The length of the spacer can be controlled easily by varying the length of the alkyl chain of the spacer. For example, also usable is a 3-hydroxybutyrate as the spacer.

Tetrabenzyl-2-hydroxyethyloxyglucoside is prepared by binding a spacer, glycolate such as ethyl glycolate to tetrabenzylglucose, which is obtained from a starting compound of glucose in an ordinary manner, to give an ester, followed by reducing it into the alcohol compound, and is represented by the following formula:

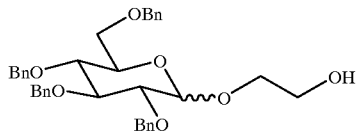

One example of the method for producing tetrabenzyl-2-hydroxyethyloxyglucoside is mentioned below.

(4)

Precisely, the ethyl ester (compound (2) having a molecular weight of 626.76) previously obtained by reacting tetra-benzylglucose with ethyl glycolate is reacted with lithium aluminum hydride in tetrahydrofuran (THF) at 0 to 100° C. for 0.5 to 50 hours, preferably for 3 hours to obtain the corresponding alcohol compound (4). This is the intended tetrabenzyl-2-hydroxyethyloxyglucoside.

Using any other saccharides in place of glucose in this reaction gives corresponding saccharide-modified products having different saccharides, as so mentioned hereinabove. Usable saccharides include, for example, mannose and galactose, in addition to glucose.

In the present invention, used is a glycolate such as ethyl glycolate as the spacer for the saccharide donor. Like that for tetrabenzyl-acetic acid-oxyglucoside mentioned above, the length of the spacer can be controlled easily by varying the length of the alkyl chain of the spacer. For example, also usable is a 3-hydroxybutyrate as the spacer.

The ursodeoxycholic acid derivatives of the present invention can be produced by reacting ursodeoxycholic acid with tetrabenzyl-acetic acid-oxyglucoside. The present invention is concretely described below, with reference to its embodiments using glucose as the saccharide.

One embodiment of producing ursodeoxycholic acid-derivatives comprises the following reaction scheme (I):

Reaction Scheme (I):

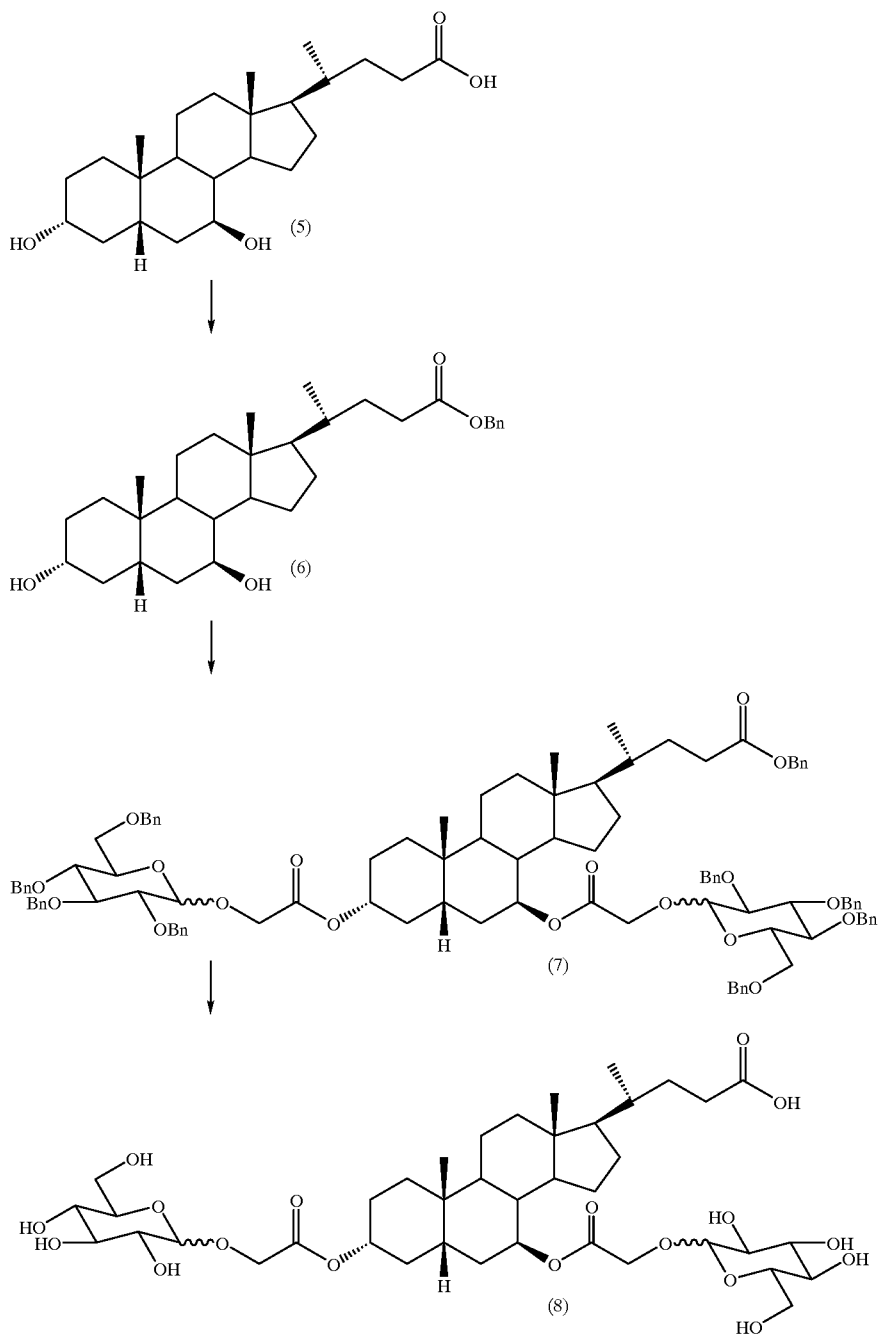

Precisely, N,N-dimethylformamide (DMF), cesium carbonate and benzyl bromide are added to ursodeoxycholic acid (5), and reacted at 0 to 60° C., preferably at 20° C. for 1 to 100 hours, preferably for 10 hours to obtain ursodeoxycholic acid (6) of which the carboxyl group is protected with a benzyl group. To the compound (6), added are tetrabenzyl-acetic acid-oxyglucoside, 4-dimethylaminopyridine (DMAP), 1-ethyl-3-(3-dimethylaminopropyl)carbodiimide hydrochloride (EDCI), and methylene chloride, and reacted at 0 to 100° C., preferably at 20° C. for 0.5 to 100 hours, preferably for 12 hours to obtain a compound (7).

Next, palladium black and acetic acid are added to the compound (7) and vigorously stirred in a hydrogen atmosphere at 0 to 60° C., preferably at 40° C. for 3 to 100 hours, preferably for 12 hours to obtain the intended compound (8). This compound (8) is 3,7-GLG-ursodeoxycholic acid as is represented by the formula noted above.

Reducing the amount of tetrabenzyl-acetic acid-oxyglucoside added in the reaction (I) gives an ursodeoxycholic acid derivative having tetrabenzyl-acetic acid-oxyglucoside as introduced thereinto only at its 3-hydroxyl group, as in the following reaction scheme (II). Ursodeoxycholic acid is one type of bile acids and has two hydroxyl groups in the molecule at its 3- and 7-positions, in which the reactivity of those hydroxyl groups is not equivalent but the reactivity of the 3-hydroxyl group is higher than that of the 7-hydroxyl group, as so described by G. Wess et al., in "Tetrahedron Letters", 33, 2, 195 (1992), by Kou-Yi Tserng and Peter D. Klein in "Steroids", 33, 2, 167 (1979), and by Sebastien Gouin and X.X. Zhu in "Steroids", 61, 11, 664 (1996). For the compounds having plural hydroxyl group of which the reactivity differs, as described by J. W. Van Cleve, in "Methods Carbohydr. Chem.", 2, 237 (1963) and by J. Gareggand Stefan Oscarson, in "Carbohydrate Research", 137, 270 (1985), the amount of the reagent to be reacted with the hydroxyl groups may be varied to make all the hydroxyl groups completely reacted with the reagent or to make a part them selectively non-reacted, thereby giving different products.

The following reaction scheme (II) indicates one typical embodiment of the present invention in which is used glucose as the saccharide.

Precisely, to the compound (6) obtained in one step of the previous reaction scheme (I), added are about 0.8 equivalent, relative to the compound (6), of tetrabenzyl-acetic acid-oxyglucoside, 4-dimethylaminopyridine (DMAP), 1-ethyl-3-(3-dimethylaminopropyl) carbodiimide hydrochloride (EDCI), and methylene chloride, and reacted at 0 to 100° C., preferably at 20° C. for 0.5 to 100 hours, preferably for 22 hours to obtain a compound (9).

Next, palladium black and acetic acid are added to the compound (9) and vigorously stirred in a hydrogen atmosphere at 0 to 60° C. preferably at 40° C. for 3 to 100 hours, preferably for 12 hours to obtain the intended compound (10). This compound (10) is 3-GLG-ursodeoxycholic acid as is represented by the formula described above.

In the following reaction scheme (III), ursodeoxycholic acid is protected only at its 3-position, and then tetrabenzyl-acetic acid-oxyglucoside is introduced thereinto at its 7-hydroxyl group to obtain an ursodeoxycholic acid derivative. One typical embodiment of this process of the invention is mentioned below, in which is used glucose as the saccharide.

Reaction Scheme (II):

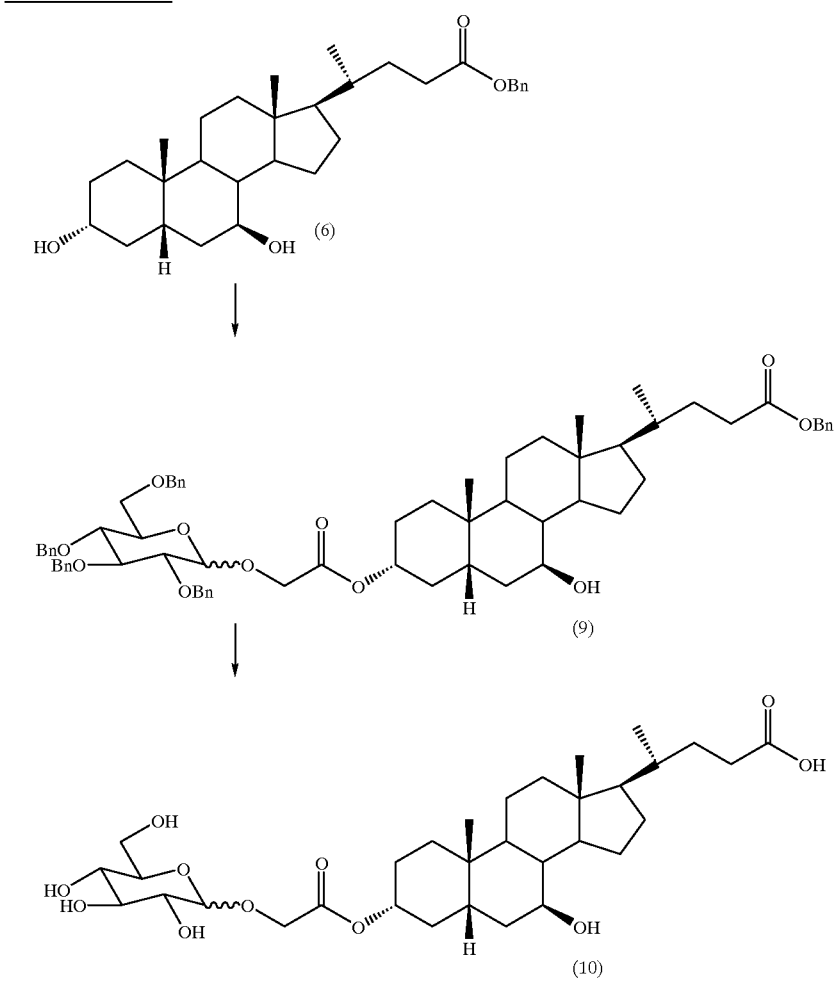

Reaction Scheme (III):

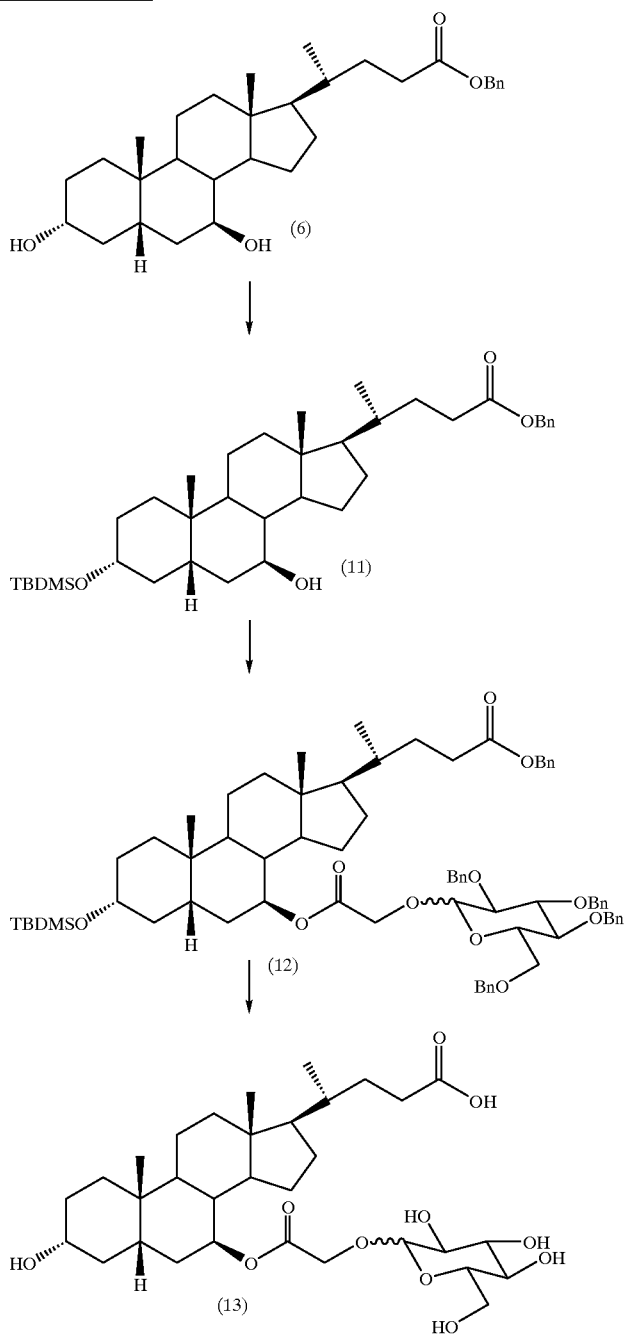

Precisely, to the compound (6) obtained in one step of the previous reaction scheme (I), added are pyridine, 4-dimethylaminopyri dine (DMAP), methylene chloride, and about 0.8 equivalent, relative to the compound (6), of t-butyldimethylsilyl chloride, and reacted at 0 to 60° C., preferably at 20° C. for 1 to 50 hours, preferably for 18 hours to obtain a compound (11) of which the 3-hydroxyl group is protected.

To the compound (11), added are tetrabenzyl-acetic acid-oxyglucoside, 4-dimethylaminopyridine (DMAP), 1-ethyl-3-(3-dimethylaminopropyl)carbodiimide hydrochloride (EDCI), and methylene chloride, and reacted at 0 to 100° C., preferably at 20° C., for 0.5 to 100 hours, preferably for 22 hours to obtain a compound (12).

Next, to the compound (12), added are pyridine hydrofluoride, pyridine and tetrahydrofuran (THF), and reacted at 0 to 60° C., preferably at 20° C. for 0.5 to 100 hours, preferably for 12 hours. Then, the reaction mixture is poured into water, extracted with ethyl acetate, and concentrated, to which are added acetic acid and palladium black and then vigorously stirred in a hydrogen atmosphere at 0 to 60° C., preferably at 40° C. for 1 to 50 hours, preferably for 12 hours to obtain the intended compound (13). This compound (13) is 7-GLG-ursodeoxycholic acid of the formula noted above.

In the following reaction scheme (IV), ursodeoxycholic acid is reacted with tetrabenzyl-2-hydroxyethyloxyglucoside to produce the ursodeoxycholic acid derivative of the present invention. One typical embodiment of this process of the invention is mentioned below, in which is used glucose as the saccharide.

sphere at 0 to 60° C., preferably at 40° C. for 1 to 50 hours, preferably for 12 hours to obtain the intended compound (16). This compound (16) is 24-GLG-ursodeoxycholic acid of the formula noted above.

The solubility in water of these ursodeoxycholic acid derivatives is improved. For example, the solubility in water Reaction Scheme (IV):

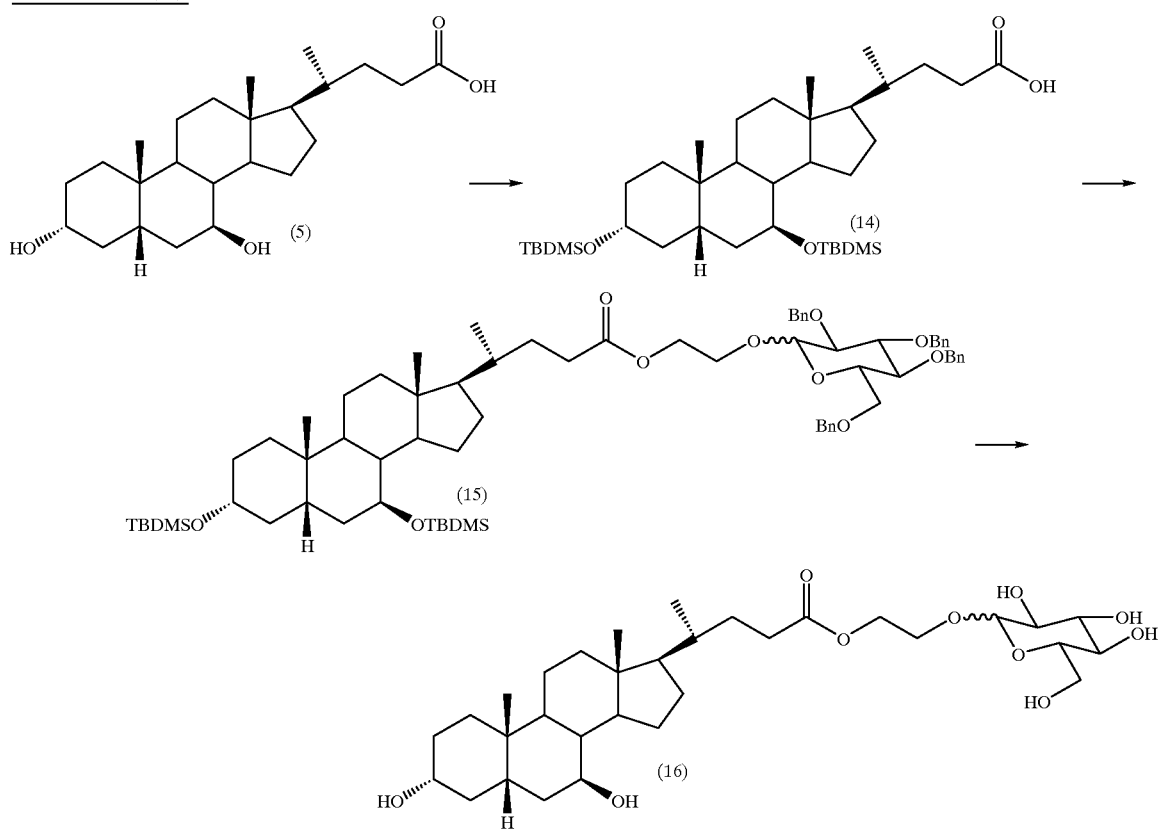

Precisely, ursodeoxycholic acid (5) and imidazole are dissolved in methylene chloride, to which are added N,N-dimethylformamide (DMF), diisopropylethylamine and t-butyldimethylsilyl chloride. After having been reacted at 0 to 60° C., preferably at 20° C. for 1 to 100 hours, preferably for 10 hours, the reaction mixture is poured into a saturated saline solution, extracted with ether, concentrated, and dissolved in methanol and tetrahydrofuran (THF). Potassium carbonate is added thereto, and reacted at 0 to 60° C., preferably at 20° C. for 1 to 100 hours, preferably for 10 hours to obtain an ursodeoxycholic acid (14) of which the hydroxyl groups are protected.

To the compound (14), added are tetrabenzyl-2-hydroxyethyloxyglu coside, 4-dimethylaminopyridine (DMAP), 1-ethyl-3-(3-dimethylaminopropyl)carbodiimide hydrochloride (EDCI), and methylene chloride, and reacted at 0 to 100° C., preferably at 20° C. for 0.5 to 100 hours, preferably for 2 hours to obtain a compound (15).

Next, to the compound (15), added are pyridine hydrofluoride, pyridine and tetrahydrofuran (THF), and reacted at 0 to 60° C., preferably at 20° C. for 0.5 to 100 hours, preferably for 12 hours. Then, the reaction mixture is poured into water, extracted with ethyl acetate, and concentrated. To the resulting concentrate, added are acetic acid and palladium black, and vigorously stirred in a hydrogen atmoof 24-GLG-ursodeoxycholic acid is 511 $\mu$g/ml, which is about 13 times that of ursodeoxycholic acid of being 38 $\mu$g/ml; and the solubility in water of 3,7-GLG-ursodeoxycholic acid is 95 mg/ml, which is about 2500 times that of ursodeoxycholic acid (38$\mu$g/ml).

The present invention provides ursodeoxycholic acid derivatives of which the solubility in water is much increased, and also methods for producing-the derivatives. The derivatives are usable in injections, and their applications as medicines are much broadened.

EXAMPLES

Now, the present invention is described in more detail hereinunder with reference to the following Examples, which, however, are not intended to restrict the scope of the invention.

PRODUCTION EXAMPLE 1

4.05 g of 2,3,4,6-tetrabenzylglucose (compound (1), $C_{34}H_{36}O_6$, having a molecular weight of 540.65) as obtained in an ordinary manner, 3.90 ml of ethyl glycolate, 0.25 g of p-toluenesulfonic acid and 150 ml of benzene were reacted for 8 hours under reflux at 110° C. to obtain an ester (compound (2), $C_{38}H_{42}O_8$, having a molecular weight of 626.74).

Next, 4.70 g of this compound was reacted with 25 ml of 6N NaOH, 25 ml of methanol and 37.5 ml of dioxane at room temperature for 3 hours, and then de-methylated in 200 ml of 1N HCl to obtain a carboxylic acid compound (compound (3), $C_{36}H_{38}O_8$, having a molecular weight of 598.69).

This carboxylic acid compound was dissolved in heavy chloroform, and analyzed through $^1$H-NMR, and its structure was identified on the basis of the peaks appearing in the $^1$H-NMR pattern to have the structural formula noted above.

PRODUCTION EXAMPLE 2

2.85 g of the ester (2) obtained in Production Example 1 was dissolved in 40 ml of tetrahydrofuran (THF), to which was gradually added 190 mg of lithium aluminum hydride in an ice bath, and reacted at 0° C. for 1 hour and then at room temperature for 2 hours to obtain an alcohol compound (compound (4), $C_{36}H_{40}O_7$, having a molecular weight of 584.71).

This alcohol compound was dissolved in heavy chloroform, and analyzed through $^1$H-NMR, and its structure was identified on the basis of the peaks appearing in the $^1$H-NMR pattern to have the structural formula noted above.

Example 1

1.178 g of ursodeoxycholic acid (5) ($C_{24}H_{40}O_4$, having a molecular weight of 392.58), 393 μl of benzyl bromide, 2.932 g of cesium carbonate, and 10 ml of N,N-dimethylformamide (DMF) were reacted in argon at 0° C. to room temperature for 24 hours to obtain a compound (6) of ursodeoxycholic acid of which the carboxyl group was protected with a benzyl group ($C_{31}H_{46}O_4$, having a molecular weight of 482.70).

To 241 mg of the compound (6), added were 718 mg of tetrabenzyl-acetic acid-oxyglucoside as obtained in Production Example 1, 244 mg of 4-dimethylaminopyridine (DMAP), 383 mg of 1-ethyl-3-(3-dimethylaminopropyl)carbodiimide hydrochloride (EDCI), and 6 ml of methylene chloride, and reacted in argon at room temperature for 12 hours to obtain a 3,7-glycosidated compound (7) ($C_{108}H_{118}O_{18}$, having a molecular weight of 1644.05).

Next, to 625 mg of the compound (7), added were 200 mg of palladium black and 5 ml of acetic acid, and vigorously stirred in a hydrogen atmosphere at 40° C. for 12 hours thereby de-benzylating the compound (7) to obtain 3,7-GLG-ursodeoxycholic acid (8) ($C_{40}H_{64}O_{18}$, having a molecular weight of 832.93).

This ursodeoxycholic acid derivative was dissolved in a heavy methanol/heavy chloroform (1/1) solution, and analyzed through $^1$H-NMR, and its structure was identified on the basis of the peaks appearing in the $^1$H-NMR pattern to have the structural formula noted above. The data are shown below.

$^1$H-NMR of 3,7-GLG-ursodeoxycholic acid (500 MHz, $CD_3OD/CDCl_3=1/1$): 0.70 (s, 3H), 0.96 (bs, 3H), 1.01 (s, 3H), 1.10–2.02 (m, 24H), 2.2–2.40 (m, 2H), 3.30–4.95 (m, 20H)

Example 2:

To 241 mg of the compound (6) as obtained in Example 1, added were 240 mg of tetrabenzyl-acetic acid-oxyglucoside (3) obtained in Production Example 1, 73 mg of 4-dimethylaminopyridine (DMAP), 115 mg of 1-ethyl-3-(3-dimethylaminopropyl)carbodiimide hydrochloride (EDCI), and 6 ml of methylene chloride, and reacted in argon at room temperature for 12 hours to obtain a 3-glycosidated compound (9) ($C_{67}H_{82}O_{11}$, having a molecular weight of 1063.38).

Next, to 168 mg of the compound (9), added were 150 mg of palladium black and 3 ml of acetic acid, and vigorously stirred in a hydrogen atmosphere at 40° C. for 12 hours thereby de-benzylating the compound (9) to obtain 3-GLG-ursodeoxycholic acid (10) ($C_{32}H_{52}O_{11}$, having a molecular weight of 612.76).

This ursodeoxycholic acid derivative was dissolved in a heavy methanol/heavy chloroform (1/1) solution, and analyzed through $^1$H-NMR, and its structure was identified on the basis of the peaks appearing in the $^1$H-NMR pattern to have the structural formula noted above. The data are shown below.

$^1$H-NMR of 3-GLG-ursodeoxycholic acid (500 MHz, $CD_3OD/CDCl_3=1/1$): 0.69 (s, 3H), 0.95 (bs, 3H), 0.98 (bs, 3H), 1.00–2.02 (m, 24H), 2.2–2.40 (m, 2H), 3.00–5.25 (m, 20H)

Example 3

To 589 mg of the compound (6) as obtained in Example 1, added were 162 μl of pyridine, 3 ml of a methylene chloride solution of 13 mg of 4-dimethylaminopyridine (DMAP), and 151 mg of t-butyldimethylsilyl chloride, and reacted at room temperature for 18 hours to obtain a compound (11) of which the 3-hydroxyl group was protected with a t-butyldimethylsilyl group (TBDMS) ($C_{37}H_{60}O_4Si$, having a molecular weight of 596.96).

Next, to 453 mg of the compound (11), added were 599 mg of tetrabenzyl-acetic acid-oxyglucoside (3) obtained in Production Example 1, 244 mg of 4-dimethylaminopyridine (DMAP), 383 mg of 1-ethyl-3-(3-dimethylaminopropyl)carbodiimide hydrochloride (EDCI), and 6 ml of methylene chloride, and reacted in argon at room temperature for 22 hours to obtain a 7-glycosidated compound (12) ($C_{73}H_{96}O_{11}Si$, having a molecular weight of 1177.64).

Next, to 100 mg of the compound (12), added were 100 mg of pyridine hydrofluoride, 3 ml of pyridine, and 3 ml of tetrahydrofuran (THF), and reacted at room temperature for 12 hours. Then, the reaction mixture was poured into 20 ml of water, extracted with ethyl acetate, and concentrated. To the resulting concentrate, added were 150 mg of palladium black and 3 ml of acetic acid, and vigorously stirred in a hydrogen atmosphere at 40° C. for 12 hours thereby de-benzylating the compound (12) to obtain 7-GLG-ursodeoxycholic acid (13) ($C_{32}H_{52}O_{11}$, having a molecular weight of 612.76).

This ursodeoxycholic acid derivative was dissolved in a heavy methanol/heavy chloroform (1/1) solution, and analyzed through $^1$H-NMR, and its structure was identified on the basis of the peaks appearing in the $^1$H-NMR pattern to have the structural formula noted above. The data are shown below.

$^1$H-NMR of 7-GLG-ursodeoxycholic acid (500 MHz, $CD_3OD/CDCl_3=1/1$): 0.70 (s, 3H), 0.98 (bs, 3H), 1.08 (bs, 3H), 1.00–2.08 (m, 24H), 2.2–2.40 (m, 2H), 3.30–4.95 (m, 20H)

Example 4

790 mg of ursodeoxycholic acid (5) and 820 mg of imidazole were dissolved in methylene chloride, to which were added 0.5 ml of N,N-dimethylformamide (DMF), and 0.52 ml of diisopropylethylamine. Then, a solution of 910 mg of t-butyldimethylsilyl chloride as dissolved in 5 ml of methylene chloride was added thereto, and reacted at room temperature for 10 hours. The reaction mixture was poured into a saturated saline solution, extracted with ether, concentrated, and dissolved in 5 ml of methanol and 10 ml of tetrahydrofuran (THF). 300 mg of potassium carbonate was added thereto, and reacted at room temperature for 3 hours to obtain an ursodeoxycholic acid (14) of which the hydroxyl groups were protected with a t-butyldimethylsilyl group (TBDMS) ($C_{36}H_{68}O_4Si_2$, having a molecular weight of 621.10).

To this compound (14), added were 240 mg of tetrabenzylethanol-oxyglucoside (4) obtained in Production Example 2, 670 mg of 4-dimethylaminopyridine (DMAP), 110 mg of 1-ethyl-3-(3-dimethylaminopropyl)carbodiimide hydrochloride (EDCI), and 7 ml of methylene chloride, and reacted at room temperature for 2 hours to obtain a carboxyl-glycosidated compound (15) ($C_{72}H_{106}O_{10}Si_2$, having a molecular weight of 1187.80).

Next, to 421 mg of this compound (15), added were 100 mg of pyridine hydrofluoride, 3 ml of pyridine. and 3 ml of tetrahydrofuran (THF), and reacted at room temperature for 12 hours. Then, the reaction mixture was poured into 20 ml of water, extracted with ethyl acetate, and concentrated. To the resulting concentrate, added were 3 ml of acetic acid and 150 mg of palladium black, and vigorously stirred in a hydrogen atmosphere at 40° C. for 12 hours thereby de-benzylating the compound (15) to obtain 24-GLG-ursodeoxycholic acid (16) ($C_{32}H_{54}O_{10}$, having a molecular weight of 598.77).

This ursodeoxycholic acid derivative was dissolved in heavy chloroform, and analyzed through $^1$H-NMR, and its structure was identified on the basis of the peaks appearing in the $^1$H-NMR pattern to have the structural formula noted above. The data are shown below.

$^1$H-NMR of 24-GLG-ursodeoxycholic acid (500 MHz, CDCl$_3$): 0.65 (s, 3H), 0.85 (9H), 0.9 (s, 9H), 0.8–2.5 (26H), 3.2–4.3 (22H), 4.78 (1H)

Example 5

20 mg of the ursodeoxycholic acid derivative prepared above and shown in Table 1 below was sampled, to which was added 0.2 ml of water and stirred for 18 hours. The resulting supernatant was taken out through filtration with a membrane filter (0.45μm), and analyzed according to the phenol-sulfuric acid method and through HPLC. The data indicating the solubility in water of the sample compound are shown in Table 1. The condition for HPLC was as follows:

Column: YMC's YMC-Pack ODS-AQ-303 (4.6×250 mm)
Solvent: CH$_3$CN/H$_2$O (50/50)
Flow Rate: 0.5 ml/min
Detector: Photo-diode array detector (202 nm)

Amount Charged into Column: 20 μl

TABLE 1

| Sample | Solubility in Water |
| --- | --- |
| Ursodeoxycholic Acid | 38 μg/ml |
| 3,7-GLG-Ursodeoxycholic Acid | 95 mg/ml |
| 24-GLG-Ursodeoxycholic Acid | 511 μg/ml |

As is obvious from the data in Table 1, the solubility in water of 24-GLG-ursodeoxycholic acid and 3,7-GLG-ursodeoxycholic acid is much higher by about 13 times and about 2500 times, respectively, than that of ursodeoxycholic acid.

While the invention has been described in detail and with reference to specific embodiments thereof, it will be apparent to one skilled in the art that various changes and modifications can be made therein without departing from the spirit and scope thereof.

The entire disclosure of Japanese Patent Application No. 10-13172 filed on Jan. 8, 1998 including specification, claims and summary are incorporated herein by reference in its entirety.

What is claimed is:

1. An ursodeoxycholic acid derivative comprising a saccharide linked to ursodeoxycholic acid by a spacer, wherein the spacer is a $C_{1-4}$ alkyl dioxyradical which has a skeletal parent containing one hydroxyl group and one carboxyl group, or alternatively, is a $C_{1-4}$ alkyl dioxyradical which has a skeletal parent containing two hydroxyl groups and the saccharide is linked to the spacer by an ether group.

2. An ursodeoxycholic acid derivative as in claim 1, wherein the saccharide is linked to ursodeoxycholic acid by a glycolic acid dioxyradical.

3. An ursodeoxycholic acid derivative as in claim 1, wherein the saccharide is linked to ursodeoxycholic acid by an ethylene glycol dioxyradical.

4. A diglycosyloxyacetyl-3,7-ursodeoxycholic acid of the formula:

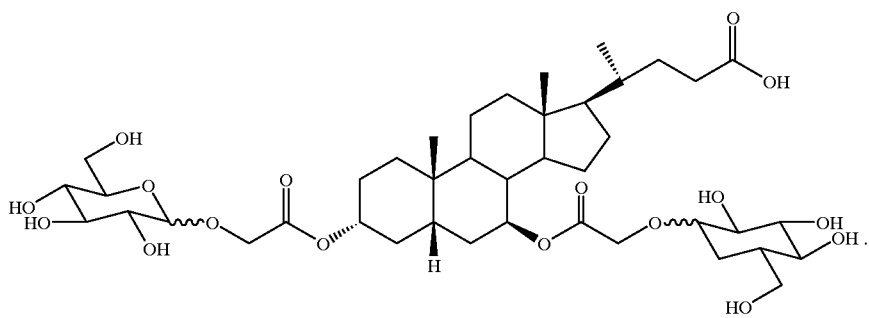

5. A glycosyloxyacetyl-3-ursodeoxycholic acid of the formula:

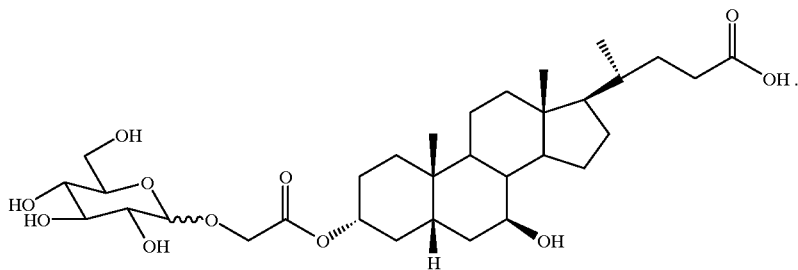

6. A glycosyloxyacetyl-7-ursodeoxycholic acid of the formula:

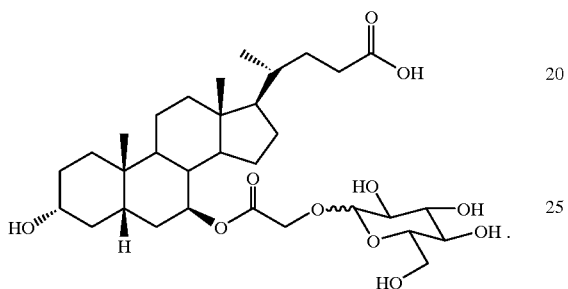

7. A glycosyloxyacetyl-24-ursodeoxycholic acid of the formula:

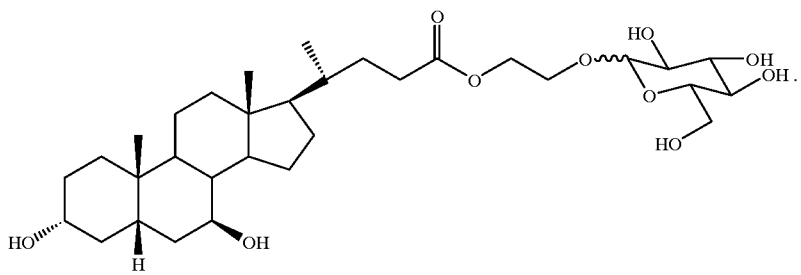

8. A method for producing ursodeoxycholic acid derivatives of any of claims 4 to 6, comprising protecting the carboxyl group of ursodeoxycholic acid with a benzyl group, then reacting the acid with tetrabenzylacetic acid-oxyglucoside of the following formula, followed by removal of all of the benzyl groups by contacting the compound thus formed with a reduction catalyst and a hydrogen donor

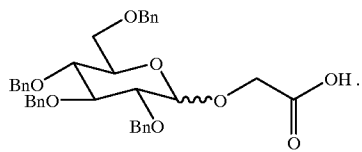

9. A method for producing an ursodeoxycholic acid derivative of claim 7, comprising protecting the hydroxyl groups in the 3 and 7 position of ursodeoxycholic acid with t-butyldimethylsilyl groups, then reacting the acid with tetrabenzyl-2-hydroxyethyloxyglucoside of the following formula, and followed by removal of all of the benzyl groups by contacting the compound thus formed with a reduction catalyst and a hydrogen donor and removal of all of the t-butyldimethylsilyl groups by contacting the compound thus formed with a source of fluoride ion

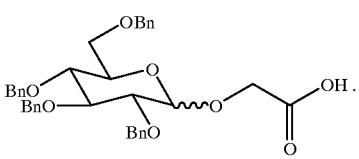

* * * * *